US010215715B1

(12) United States Patent
Cory et al.

(10) Patent No.: US 10,215,715 B1
(45) Date of Patent: Feb. 26, 2019

(54) SPIN-ORBIT STATES OF NEUTRON WAVE PACKETS

(71) Applicant: QUANTUM VALLEY INVESTMENT FUND LP, Waterloo (CA)

(72) Inventors: David G. Cory, Branchton (CA);
Joachim Nsofini, Waterloo (CA);
Dusan Sarenac, Waterloo (CA);
Dmitry A. Pushin, Boston, MA (US)

(73) Assignee: Quantum Valley Investment Fund LP, Waterloo, Ontario ( * ) Notice: Subject to any disclaimer, the term of this patent is extended or adjusted under 35 U.S.C. 154(b) by 196 days.

(21) Appl. No.: 15/277,190

(22) Filed: Sep. 27, 2016

(51) Int. Cl.
*G01N 23/02* (2006.01)

(52) U.S. Cl.
CPC ....... *G01N 23/025* (2013.01); *G01N 2223/30* (2013.01)

(58) Field of Classification Search
CPC .................... G01N 23/025; G01N 2223/30
See application file for complete search history.

(56) References Cited

U.S. PATENT DOCUMENTS

| | | | | |
|---|---|---|---|---|
| 2008/0217533 | A1* | 9/2008 | Kohashi | G01N 23/2251 250/310 |
| 2014/0252240 | A1* | 9/2014 | Baker | G01N 23/005 250/370.05 |
| 2015/0323473 | A1* | 11/2015 | Mitra | G01N 23/025 250/390.04 |
| 2018/0166500 | A1* | 6/2018 | Wang | H01L 27/224 |

OTHER PUBLICATIONS

C. W. Clark, R. Barankov, M. G. Huber, M. Arif, D. G. Cory, and D. A. Pushin, Controlling neutron orbital angular momentum; Nature 525, pp. 504; 7 pages (Sep. 2015).
A. M. Yao and M. J. Padgett, Orbital angular momentum: origins, behavior and applications; Adv. Opt. Photonics 3, pp. 161-204; 45 pages (2011).
A. Mair, A. Vaziri, G. Weihs, and A. Zellinger, Entanglement of the orbital angular momentum states of photons; Nature 412, pp. 313-316; 4 pages (Jul. 2001).
A. Muthukrishnan and C. R. S. Jr, Entanglement of internal and external angular momenta of a single atom; Journal of Optics B: Quantum and Semiclassical Optics 4, S73-S77 5 pages (2002).
D. A. Pushin, M. Arif, M. G. Huber, and D. G. Cory, Measurments of the Vertical Coherence Length in Neutron Interferometry; Phys. Rev. Lett. 100, 250404 4 pages; (Jun. 2008).

(Continued)

*Primary Examiner* — Rodney A Bonnette
(74) *Attorney, Agent, or Firm* — Henry Patent Law Firm PLLC

(57) ABSTRACT

In a general aspect, the spin angular momentum of a neutron wave packet is coupled with the orbital angular momentum of the neutron wave packet. In some instances, an initial state of a neutron wave packet is generated. The neutron wave packet in the initial state has a spin angular momentum that is polarized in an axial direction. The neutron wave packet is directed through a quadrupole magnetic field that couples the spin angular momentum of the neutron wave packet with an orbital angular momentum of the neutron wave packet. A spin-orbit state of the neutron wave packet is produced from the quadrupole magnetic field.

19 Claims, 3 Drawing Sheets

(56) References Cited

OTHER PUBLICATIONS

E. Karimi, J. Leach, S. Slussarenko, B. Piccirillo, L. Marrucci, L Chen, W. She, S. Franke-Arnold, M. J. Padgett, and E. Santamato, Spin-orbit hybrid entanglement of photons and quantum contextuality; Phys. Rev. A 82, 022115; 4 pages (2010).

E. Karimi, L. Marrucci, V. Grillo, and E. Santamato, Spin-to-Orbital Angular Momentum Conversion and Spin-Polarization Filtering in Electron Beams; Phys. Rev. Lett. 108, 044801; 5 pages; (Jan. 2012).

E. Santamato, Photon orbital angular momentum: problems and perspectives; Fortschritte der Physik 52, 1141-1153; 13 pages; (2004).

F. Cardano and L. Marrucci, Spin-Orbit Photonics; Nature Photonics 9, 776; 3 pages; (Dec. 2015).

G. Guzzinati, L. Clark, A. Beche, and J. Verbeeck, Measuring the orbital angular momentum of electron beams; Phys. Rev. A 89, 025803; 5 pages; (Feb. 2014).

J. Harris, V. Grillo, E. Mafakheri, G. C. Gazzadi, S. Frabboni, R. W. Boyd, and E. Karimi, Structured quantum waves; Nature Physics 11, 629-634 (Jul. 2015).

L. Allen, M. W. Beijersbergen, R. J. C. Spreeuw, and J. P. Woerdman, Orbital angular momentum of light and the transformation of Laguerre-Gaussian laser modes; Phys. Rev. A 45, 8185-8189; 5 pages (Jun. 1992).

L. Marrucci, C. Manzo, and D. Paparo, Optical Spin-to-Orbital Angular Momentum Conversion in Inhomogenious Anisotropic Media; Phys. Rev. Lett. 96; 163905; 4 pages, (Apr. 2006).

N.F. Ramsey, A Molecular Beam Resonance Method with Separated Oscillating Fields; Phys. Rev. 78, No. 6, pp. 695-699; 5 pages (Jun. 1950).

P. Rungta, V. Bužek, C. M. Caves, M. Hillery, and G. J. Milburn, Universal state inversion and concurrence in arbitrary dimensions; Phys. Rev. A 64, 042315; 13 pages, (2001).

R. W. Boyd, Neutrons with a twist; Nature 525, 462-464; 3 pages (Sep. 2015).

S. Albeverio and S.-M. Fei, A note on invariants and entanglements; Journal of Optics B: Quantum and Semiclassical Optics 3, 223-227; 6 pages; (Jul. 2001).

S. Hill and W. K. Wootters, Entanglement of a Pair of quantum Bits; Phys. Rev. Lett. 78, No. 26; 5022-5025; 4 pages; (Jun. 1997).

V. F. Sears, Neutron Optics: An Introduction to the Theory of Neutron Optical Phenomena and their Applications; pp. 52-57 (Oxford University Press, New York, Mar. 1989).

V. Grillo, L. Marrucci, E. Karimi, R. Zanella, and E. Santamato, Quantum simulation of a spin polarization device in an electron microscope; New Journal of Physics 15, 093026; 26 pages (Sep. 2013).

V. S. Liberman and B. Y. Zel'dovich, Spin-orbit interaction of a photon in an inhomogeneous medium; Phys. Rev. A 46, 5199; 9 pages (Oct. 1992).

W. K. Wootters, Entanglement of Formation of an Arbitrary State of Two Qubits; Phys. Rev. Lett. 80, No. 10; 2245-2248; 4 pages (Mar. 1998).

Z. Bomzon, G. Biener, V. Kleiner, and E. Hasman, Space-Variant Pancharatnam-Berry phase optical elements with computer-generated subwavelength gratings; Opt. Lett. 27, 1141-1143; 3 pages (Jul. 2002).

R. Shiloh, Y. Tsur, R. Remez, Y. Lereah, B. A. Malomed, V. Shvedov, C. Hnatovsky, W. Krolikowski, and A. Arie, Unveiling the orbital angular momentum and acceleration of electron beams; arXiv:1402.3133v1; Phys. Rev. Lett. 114, 096102; 12 pages (Feb. 2015).

J. F. Nye and M. V. Berry, Dislocations in wave trains; Procs R. Soc. of Lond. A, Mathematical and Physical Sciences 336, pp. 165-190; 26 pages (1974).

Nsofini et al.; Spin-Orbit States of Neutron Wavepack; Feb. 22, 2016; arXiv:1602.06644v1 [quant-ph] 13 pages.

F. W. J. Olver, D. W. Lozier, R. F. Boisvert, C. W. Clark, eds., NIST Handbook of Mathematical Functions; p. 439; (Cambridge University Press, New York, NY, 2010).

H. Rauch and S. A. Werner, Neutron Interferometry: Lessons in Experimental Quantum Mechanics, Wave-Particle Duality, and Entanglement, vol. 12; pp. 108-122; Oxford University Press; 2 edition, 2015.

J. P. Torres and L. Torner, Twisted Photons: Applications of Light with Orbital Angular Momentum; pp. 13-23 and 25-34; (Wiley-VCH, Mar. 2011).

S. L. Chuang, Physics of Photonic Devices; pp. 227-239; (Wiley, New Jersey, 2009).

Sears, Neutron Optics: An Introduction to the Theory of Neutron Optical Phenomena and their Applications; Oxford Univ. Press, New York; Mar. 1989; pp. 17-22.

W. H. Zachariasen, Theory of X-Ray Diffraction in Crystals; pp. 82-96; (Wiley, New York, 1945).

"L. Torner, J. P. Torres, and S. Carrasco, Digital spiral imaging; Optics Express 13, No. 3; 873-881; 9 pages; (Feb. 2005)".

* cited by examiner

SPIN-ORBIT STATES OF NEUTRON WAVE PACKETS

BACKGROUND

The following description relates to spin-orbit states of neutron wave packets.

Neutrons are known to support orbital angular momentum. For example, a spiral phase plate has been used to write a helical wavefront onto a neutron beam. The helical wavefront of a neutron beam can be analyzed, for instance, using neutron interferometry.

DETAILED DESCRIPTION

Figure 1:
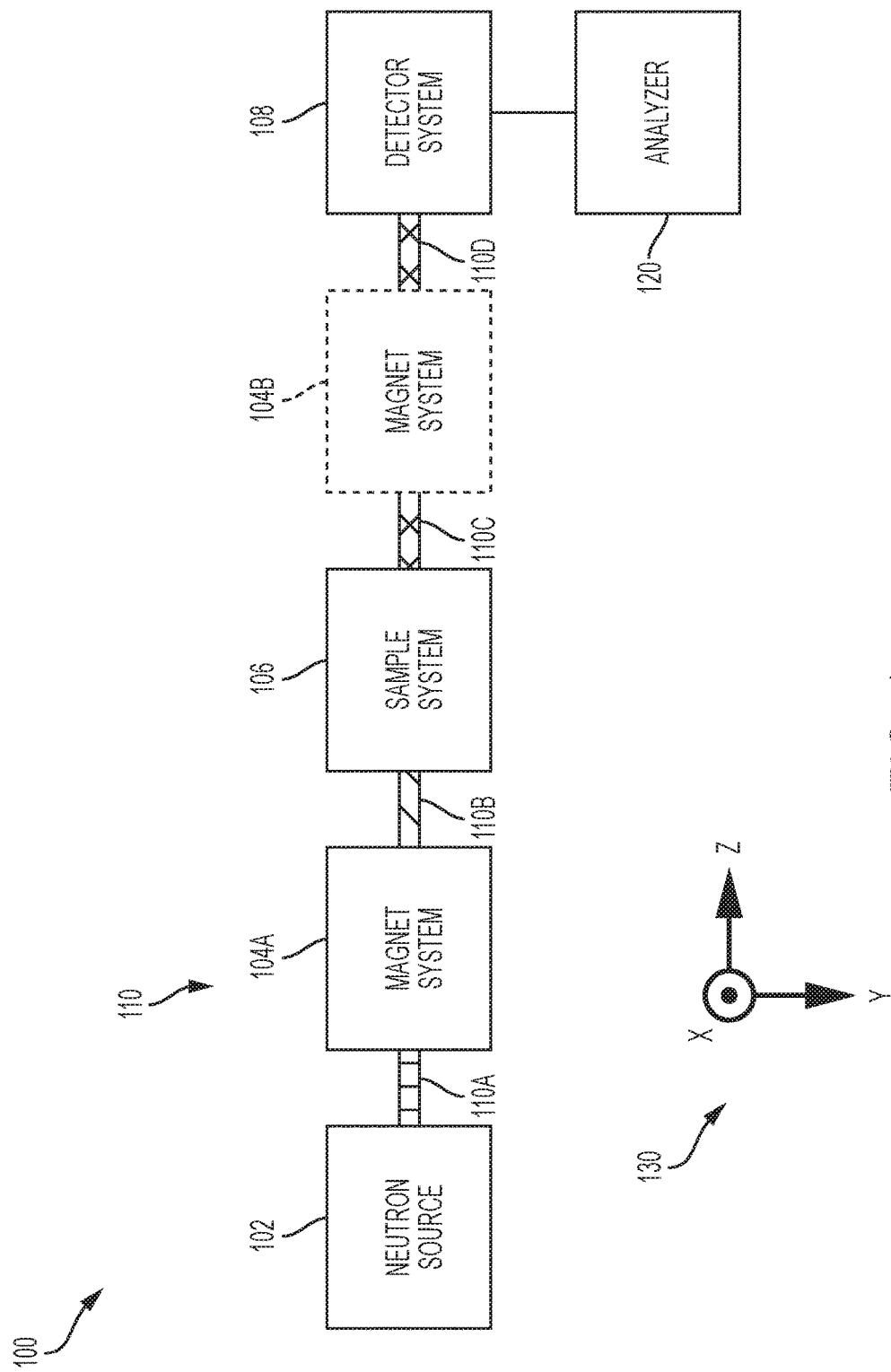
FIG. 1 is a block diagram showing an example system that can prepare a spin-orbit state of a neutron wave packet.

In some aspects of what is described here, a spin-orbit state of a neutron wave packet is prepared. In some examples, the spin-orbit state is an entangled state. The spin-orbit state can be prepared by passing a neutron wave packet through the center of a quadrupole magnetic field gradient, which creates a spin-orbit coupling. The length of the quadrupole magnetic field (e.g., the axial length in the direction of neutron wave packet propagation) and the gradient strength (e.g., the transverse gradient strength perpendicular to the direction of neutron wave packet propagation) can determine the parameters of the state produced. In some instances, the quadrupole magnetic field and the gradient strength can set to a condition that controls (and in some cases, optimizes) the concurrence between the orbital and spin degrees of freedom of the neutron wave packet. In some implementations, the spin-orbit state of the neutron wave packet can be used as a probe for studying materials, such as, for example, chiral and helical materials.

A neutron can support orbital angular momentum (OAM) and has an intrinsic spin of ½. In some implementations of what is described here, a neutron wave packet can be prepared in an spin-orbit state. In a cylindrical coordinate system $(r, \phi, z)$, the OAM operator can be expressed $$L_z = \frac{i}{\hbar}\frac{\partial}{\partial \phi},$$

where r represents the radial coordinate, $\phi$ represents the azimuthal coordinate, and z represents the axial coordinate. A neutron beam can be considered as travelling along the z-direction, with a momentum in the z-direction $k_z$ and expectation values of momentum in the transverse $(r, \phi)$ plane of zero. The eigenstates of the OAM operator can be used as a basis for a neutron wave packet, for example, when the standard deviations of momentum in the transverse directions are equal: $\sigma_x=\sigma_y=\sigma_\perp$. Here $\sigma_{x,y}=\Delta k_{x,y}$, and $\Delta k_{x,y}$ are the neutron wave packet's transverse momentum distributions.

Under this cylindrical symmetry, the neutron wave function is separable in spin and in each of the cylindrical (radial, azimuthal and longitudinal) coordinates, such that $\Psi=R(r)\Phi(\phi)Z(z)|s\rangle$, where $$|s\rangle \in \left\{ \uparrow = \begin{pmatrix} 0 \\ 1 \end{pmatrix}, \downarrow = \begin{pmatrix} 1 \\ 0 \end{pmatrix} \right\}$$

specifies the neutron spin state along the quantization axis. With the standard deviation of momentum being constant in the transverse direction, the transverse wave function $R(r)\Phi(\phi)$ may be described in terms of solutions to the two-dimensional (2D) harmonic oscillator, and the longitudinal wave function $Z(z)$ can be treated as a Gaussian wave packet. The eigenstates, denoted by $|n_r,l,k_z,s\rangle$, are specified by the radial quantum number $n_r$, the azimuthal quantum number l, the wave vector along the z-direction $k_z$, and the spin state s.

The basis states in cylindrical coordinates are:

$$|n_r, l, k_z, s\rangle = \mathcal{N}\xi^{|l|}e^{-\frac{\xi^2}{2\sigma_\perp^2}}\mathcal{L}_{n_r}^{|l|}(\xi^2)e^{-il\phi}Z(z)|s\rangle$$

where $\xi=r/\sigma_\perp$ represents the rescaled radial coordinate, $$\mathcal{N} = \frac{1}{\sigma_\perp}\sqrt{\frac{n_r!}{\pi(n_r+|l|)!}}$$

is the normalization constant, $n_r \in (0, 1, 2, \ldots)$ is the radial quantum number, $l \in (0, \pm 1, \pm 2, \ldots)$ is the angular momentum quantum number, are the associated Laguerre Polynomials. The total energy is given by $$E_T = \hbar\omega_\perp(2n_r+|l|+1) + \frac{\hbar^2 k_z^2}{2m} - \vec{\mu}\cdot\vec{B}$$

where $\vec{\mu}$ represents the neutron magnetic dipole moment, $$\omega_\perp^2 = \frac{\hbar}{2m\sigma_\perp^2},$$

represents the matter wave oscillation frequency, $\hbar$ represents the reduced Planck's constant, m represents the neutron mass and $\vec{B}$ is the external magnetic field.

In some implementations of the techniques described here, a spin-orbit state of a neutron wave packet is prepared by a process in which a spin-polarized neutron wave packet passes through the center of a quadrupole magnetic field. For a given neutron wave packet transverse coherence length, the quadrupole magnetic field gradient and the quadrupole magnetic field length can be chosen, for example, to achieve a specified or optimized concurrence between the spin and orbit degrees of freedom. In a spin-orbit state of a neutron wave packet, the spin and orbital degrees of freedom, which are represented by separate quantum numbers, have a non-trivial correlation. The spin degree of freedom of the neutron wave packet may be represented by the projection of spin along an axis (e.g., the z-axis), and the orbital degree of freedom of the neutron wave packet may be represented by an integer that describes the periodicity under a physical rotation of the state. For instance, an orbital quantum number of n indicates that the state returns to itself under a rotation of $2\pi/n$, within a global phase. Using these quantum numbers, the spin-orbit state of the neutron wave packet may have the form ($|\uparrow, n\rangle + |\downarrow, n+1\rangle$); or another class of spin-orbit states may be prepared in some implementations.

FIG. 1 is a block diagram showing an example system 100 that can prepare a spin-orbit state of a neutron wave packet. The example system 100 shown in FIG. 1 includes a series of apparatus along a neutron path 110 traversed by neutron wave packets. As shown in FIG. 1, the example system 100 includes a neutron source 102, a first magnet system 104A, a sample system 106, a second magnet system 104B, and a detector system 108 on the neutron path 110. The example system 100 also includes an analyzer 120 that can receive and analyze data (e.g., measurement data) from the detector system 108. In the example shown in FIG. 1, a neutron wave packet can propagate along the neutron path 110 in an axial direction from the neutron source 102 toward the detector system 108. A system for preparing spin-orbit states of a neutron wave packet may include additional or different features, and the components of the system may be configured as shown in FIG. 1 or they may be configured in another manner.

FIG. 1 includes a coordinate system legend 130, which shows the directions of the x-axis, y-axis and z-axis of a Cartesian coordinate system. The system 100 can also be described with reference to the cylindrical coordinate system mentioned above, which has an axial coordinate z, a radial coordinate r and an azimuthal coordinate $\phi$. In the example shown in FIG. 1, the axial coordinate z of the cylindrical coordinate system aligns with the z-axis of the Cartesian coordinate system shown in the legend 130, and the radial and azimuthal coordinates (r, $\phi$) of the cylindrical coordinate system are defined in the transverse plane (the xy-plane) of the Cartesian coordinate system shown in the legend 130. In some examples, a neutron wave packet can be described in another coordinate system.

The example neutron source 102 can be described in terms of neutron wave packets. In some examples, the neutron source 102 includes a reactor (e.g., a nuclear reactor) or another type of system that produces a neutron beam. In some instances, the example neutron source 102 can be filtered to produce spin-polarized neutron wave packets. For example, the neutron source 102 may be followed by a supermirror, a configuration of multiple supermirrors or another type of system that polarizes the spin states of neutrons produced from a reactor. In the example shown, a spin-polarized neutron wave packet produced by the neutron source 102 has a spin angular momentum that is polarized in the axial direction, parallel to the z-axis in FIG. 1. In some cases, the spin-polarized neutron wave packet can have a spin angular momentum that is polarized in another direction, for instance, along another axis.

The example magnet system 104A can generate a quadrupole magnetic field. In some examples, the quadrupole magnetic field generated by the magnet system 104A varies in the transverse directions, which are perpendicular to the z-axis. For example, the quadrupole field gradient can be described in the xy-coordinates of the Cartesian coordinate system or in the radial and azimuthal coordinates (r, $\phi$) of the cylindrical coordinate system. In the example shown in FIG. 1, the magnet system 104A defines a quadrupole magnetic field that has a central axis oriented in the z-direction, and the neutron path 110 is axially aligned with the central axis of the quadrupole magnetic field. In some cases, the quadrupole magnetic field generated by the magnet system 104A can be uniform or negligible (e.g., zero) along the z-direction.

In some cases, the quadrupole magnetic field in the magnet system 104A can be generated by permanent magnets, electromagnets, superconducting magnets or another magnet apparatus. In some cases, the magnet system 104A includes one or more permanent magnets configured to generate the quadrupole magnetic field. The permanent magnets can include, for example, neodymium (NdFeB) magnets or another magnetic material in a quadrupole arrangement.

The second magnet system 104B can generate a quadrupole magnetic field. For example, the quadrupole magnetic field generated by the second magnet system 104B can be similar to the quadrupole magnetic field generated by the first magnet system 104A. In some examples, the quadrupole magnetic field in the second magnet system 104B is a rotated version of the quadrupole magnetic field in the magnet system 104A. For instance, the quadrupole magnetic field generated by the magnet system 104B can be rotated about the z-axis with respect to the quadrupole magnetic field generated by the first magnet system 104A.

The example sample system 106 can provide a sample material on the neutron path 110. For example, the sample system 106 may support a sample material to be analyzed on the neutron path between the magnet system 104A and the detector system 108. The sample material can be, for example, a material that has chiral or helical properties that can be probed by the neutron wave packet.

The example detector system 108 can measure properties of a neutron wave packet. For example, the detector system 108 can include a Helium-3 (He-3) neutron detector or another type of detector apparatus. The analyzer 120 can include, for example, a computer system that receives and analyzes the measurement data from the detector system 108. For instance, the analyzer 120 can include memory, one or more data processors, one or more user interface devices, data ports, communication interfaces, etc. In some instances, the analyzer 120 includes software, hardware or firmware configured to digitize and process data from one or more of the detector system 108, the neutron source 102, the magnet systems 104A, 104B, the sample system 106 or other systems or components.

In some example aspects of operation of the system 100 shown in FIG. 1, a neutron wave packet in an initial state is produced from the neutron source 102 on a first portion 110A of the neutron path 110. The initial state of the neutron wave packet can be a spin-polarized state, where the spin angular momentum is polarized along the z-axis, or another initial state may be produced by the neutron source 102 in some cases. The example neutron source 102 directs the neutron wave packet along the neutron path 110 in the axial direction, through the quadrupole magnetic field in the magnet system 104A.

In some example aspects of operation, the magnet system 104A receives the neutron wave packet in the initial state, and the neutron wave packet passes through the quadrupole magnetic field, along a central axis of the quadrupole magnetic field. As the neutron wave packet passes through the quadrupole magnetic field in the magnet system 104A, the quadrupole magnetic field couples the spin angular momentum of the neutron wave packet with the orbital angular momentum of the neutron wave packet. Passing the neutron wave packet through the quadrupole magnetic field produces an output state of the neutron wave packet on a second portion 110B of the neutron path 110. In some instances, the output state of the neutron wave packet produced at 110B is a spin-orbit state in which a correlation between the spin and orbital degrees of freedom can be detected. In some examples, the spin-orbit state is in the class of states ($|\uparrow,n\rangle+|\downarrow,n+1\rangle$); in this class of states, measuring either the spin or the orbital degree of freedom projects the other (orbital or spin) degree of freedom as well. In some instances, the output state of the neutron wave packet produced at 110B is an entangled spin-orbit state in which the spin angular momentum of the neutron wave packet is entangled with the orbital angular momentum of the neutron wave packet. In some instances, another output state is produced from the magnet system 104A.

In some example aspects of operation, the output state of the neutron wave packet produced on the second portion 110B of the neutron path 110 is directed to the sample system 106. At the sample system 106, the neutron wave packet interacts with a sample on the neutron path 110. In some examples, the sample system 106 includes a chiral or helical material that can be analyzed by using the output state (e.g., an entangled spin-orbit state) of the neutron wave packet as a probe. For instance, the sample material may interact with the spin-orbit state of the neutron wave packet and thereby modify the spin-orbit state, and the modified state of the neutron wave packet may then be analyzed to obtain information about the sample material.

In some example aspects of operation, after interacting with the sample in the sample system 106, the neutron wave packet is directed toward the detector system 108. In some instances, the sample system 106 produces a modified output state on a third portion 110C of the neutron path 110, and the modified output state of the neutron wave packet is received by the second magnet system 104B. In some examples, the magnet system 104B generates a quadrupole magnetic field that couples the spin angular momentum of the neutron wave packet with the orbital angular momentum of the neutron wave packet. In the example shown in FIG. 1, the second magnet system 104B produces a final state of the neutron wave packet on a fourth portion 110D of the neutron path 110. The final state of the neutron wave packet is detected by the detector system 108. The detector system 108 generates measurement data based on the detected neutron wave packet, and the measurement data can be analyzed by the analyzer 120.

In the following discussion and in FIGS. 2 and 3, example interactions between the magnet system 104A and the neutron wave packet are analyzed. In this example, the spin angular momentum of a neutron wave packet generated by the neutron source 102 is polarized along the z-direction, and the neutron wave packet travels through a quadrupole magnetic field generated by the magnet system 104A. In this example, the quadrupole magnetic field geometry generated by the magnet system 104A can be described by the quadrupole gradient relationship $$\frac{\partial B_x}{\partial y} = -\frac{\partial B_y}{\partial x}$$

in the transverse direction, and the magnetic field generated by the magnet system 104A has zero or another negligible magnetic field component in the z-direction. The magnetic field vector in cylindrical coordinates is given by $$\vec{B}=|\nabla B|r(\cos(q\phi),\sin(q\phi),0)$$

where $|\nabla B|$ is the quadrupole gradient, r is the distance from the quadrupole's central axis, and the topological charge q=−1, which quantifies the nature of the singularity at the center of the quadrupole field. Thus, the magnitude of the magnetic field varies radially, while the direction changes azimuthally, and the magnetic field is substantially uniform or zero axially. The Hamiltonian inside the quadrupole magnetic field can be parametrized by $$H=\vec{\hat{\sigma}}\cdot\vec{B}\gamma\hbar/2$$

where $\vec{\hat{\sigma}}$ corresponds to the Pauli matrices and γ is the neutron gyromagnetic ratio.

The time a neutron spends inside the quadrupole magnetic field can be expressed $$t_Q=l_Q/v_z,$$

where $l_Q$ represents the axial length of the quadrupole magnetic field in the z-direction, and $$v_z = \frac{2\pi\hbar}{m\lambda}$$

is the velocity of the neutron. In this example, the neutron is on axis with the central axis of the quadrupole magnetic field. In this analysis, ignoring any displacement due to the gradient, the operator on the spin can be expressed $$U_Q = \exp\left(i\frac{\gamma|\nabla B|rl_q}{2v}\vec{n}\cdot\vec{\hat{\sigma}}\right)$$
$$= \cos\left(\frac{\pi r}{2r_c}\right)\mathbb{1} + i\vec{n}\cdot\vec{\hat{\sigma}}\sin\left(\frac{\pi r}{2r_c}\right)$$

where $$\vec{n}\cdot\vec{\hat{\sigma}} = (\hat{\sigma}_x\cos\phi - \hat{\sigma}_y\cos\phi)$$

and the operator in the second line has been re-parameterized with the radius $r_c$ at which the spin undergoes a spin flip on passing through the length of the quadrupole $$\frac{\gamma|\nabla B|r_c l_Q}{v} = \pi.$$

Here, the action of the quadrupole magnetic field on the neutron wave packet depends on the magnetic field length, the magnetic field gradient strength, and the neutron wavelength.

Defining the raising and lowering OAM operators $l_\pm=e^{\pm i\phi}$ and spin operators $$\hat{\sigma}_\pm = (\hat{\sigma}_x \pm i\hat{\sigma}_y)/2,$$

the operator of the quadrupole magnetic field becomes $$U_Q = \cos\left(\frac{\pi r}{2r_c}\right)\mathbb{1} + i\sin\left(\frac{\pi r}{2r_c}\right)(l_+\hat{\sigma}_+ + l_-\hat{\sigma}_-)$$

In this example expression of the operator $U_Q$, the second term represents an entangling operation between spin angular momentum and orbital angular momentum. Hence, passage of a neutron wave packet through the quadrupole magnetic field has the potential to entangle the spin and orbital degrees of freedom. Changes to the radial quantum number may also be considered.

To illustrate this example, consider the case where an arbitrary spin up polarized basis state $$\Psi_{in} = \psi_{n_i, l_i, \uparrow}$$

is incident through the center of the quadrupole magnetic field. As mention above, in this example, the quantities defining the wave function are $k_z$, $\Delta k_z$, $\sigma_\perp$, $n_r$, and $l$. Upon propagation through a quadrupole we assume that $k_z$, $\Delta k_z$, $\sigma_\perp$ are all conserved quantities. The state at the output post-selected for no change in radial quantum number is $$\Psi_Q = \cos\left(\frac{\pi r}{2r_c}\right)\psi_{n_i, l_i, \uparrow} + i\sin\left(\frac{\pi r}{2r_c}\right)\psi_{n_i, l_i+1, \downarrow}$$

which is entangled in spin and orbit degrees of freedom.

In this example, including the radial degree of freedom, the state of the neutron wave packet after exiting the quadrupole magnetic field can be expanded in the basis functions as:

$$\Psi_Q = \sum_{n_r} C_{n_r, l_i, \uparrow} \psi_{n_r, l_i, \uparrow} + i C_{n_r, l_i+1, \downarrow} \psi_{n_r, l_i+1, \downarrow}$$

where the coefficients are given by $$C_{n_r, l_i, \uparrow} = 2\sqrt{\frac{n_r! n_i!}{(n_r + |l_i|)!(n_i + |l_i|)!}} \times$$

$$\int_0^\infty \xi^{2|l_i|} e^{-\xi^2} \mathcal{L}_{n_r}^{|l_i|}(\xi^2) \mathcal{L}_{n_i}^{|l_i|}(\xi^2) \times \cos\left(\frac{\pi \sigma_\perp}{2r_c}\xi\right) \xi d\xi,$$

and $$C_{n_r, l_i+1, \downarrow} = 2\sqrt{\frac{n_r! n_i!}{(n_r + |l_i| + 1)!(n_i + |l_i|)!}} \times$$

$$\int_0^\infty \xi^{2|l_i|+1+|l_i|} e^{-\xi^2} \mathcal{L}_{n_r}^{|l_i|+1}(\xi^2) \mathcal{L}_{n_i}^{|l_i|}(\xi^2) \times \sin\left(\frac{\pi \sigma_\perp}{2r_c}\xi\right) \xi d\xi,$$

where $\xi = r/\sigma_\perp$. FIG. 2 is a plot 200 showing example coefficients $C_{n_r, l, s}$ of a spin-orbit state of a neutron wave packet for $n_r = 0$ and $n_r = 1$. For the example shown in FIG. 2, the input state into the quadrupole magnetic field is $n_{r_i} = 0$, $l_i = 0$. It can be shown that $$\sum_{n_r} (|C_{n_r, l_i, \uparrow}|^2 + |C_{n_r, l_i+1, \downarrow}|^2) = 1$$

In some implementations, the spin-orbit state at the exit of a quadrupole magnetic field is an entangled state between the OAM degree of freedom and the spin degree of freedom.

Figure 2:
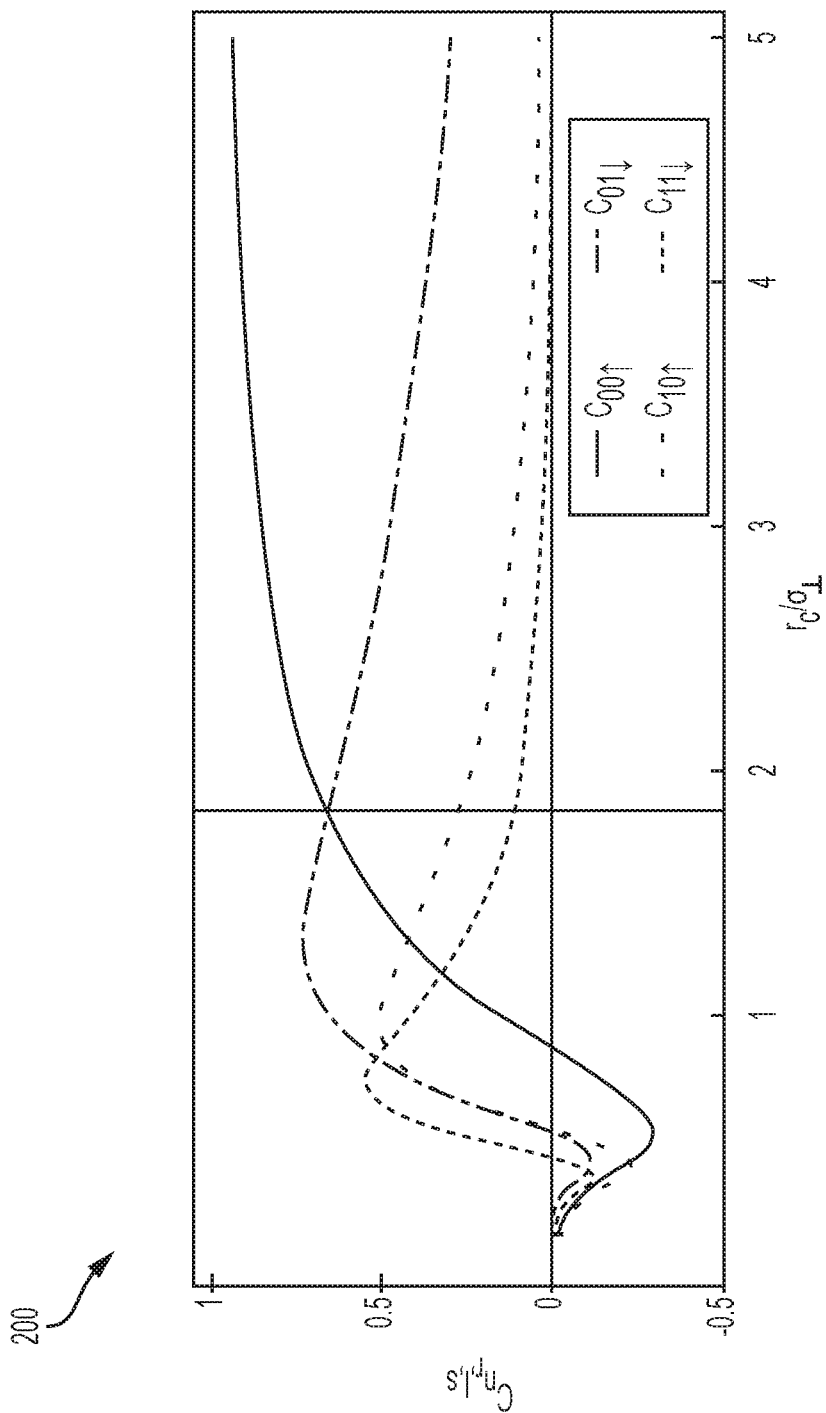
FIG. 2 is a plot showing example coefficients of a spin-orbit state of a neutron wave packet.

In the plot 200 shown in FIG. 2, the horizontal axis represents a range of values for the rescaled radial coordinate $\xi = r/\sigma_\perp$, and the vertical axis represents a range of values for the wave function coefficients $C_{n_r, l, s}$. The curves in the plot 200 represent respective calculated values for four wave function coefficients $C_{0,0,\uparrow}$ (for $n_r = 0$, $l_i = 0$ and $s = \uparrow$), $C_{1,0,\uparrow}$ (for $n_r = 1$, $l_i = 0$ and $s = \uparrow$), $C_{0,1,\downarrow}$ (for $n_r = 0$, $l_i = 1$ and $s = \downarrow$), $C_{1,1,\downarrow}$ (for $n_r = 1$, $l_i = 1$ and $s = \downarrow$).

In some instances, a useful measure of entanglement for a bipartite quantum system is the concurrence, which is equal to 1 when the entanglement is maximum and 0 when the state is separable. For a bipartite mixed state $\rho_{SO}$, the concurrence can be expressed $$\mathcal{C}(\rho_{SO}) = \max\{0, \lambda_1 - \lambda_2 - \lambda_3 - \lambda_4\}$$

where the $\lambda_i$ values are the eigenvalues, sorted in descending order, of $$\sqrt{\sqrt{\rho_{SO}}(\sigma_y \otimes \sigma_y)\rho_{SO}^*(\sigma_y \otimes \sigma_y)\sqrt{\rho_{SO}}}$$

And $\rho_{SO}^*$ is the complex conjugate of $\rho_{SO}$. For a pure state $$\rho_{SO} = |\psi_{SO}\rangle\langle\psi_{SO}|,$$

the expression for concurrence above reduces to $$\mathcal{C}(|\psi_{SO}\rangle) = \sqrt{2(1 - Tr[\rho_S^2])},$$

where $$\rho_S = Tr_O[|\psi_{SO}\rangle\langle\psi_{SO}|]$$

is the reduced density matrix obtained by tracing over the subsystem S (or equivalently tracing could be over subsystem O). In some examples, the maximum value of the concurrence $\mathcal{C} = 0.97$ is obtained at $r_c = 1.82\ \sigma_\perp$.

Figure 3:
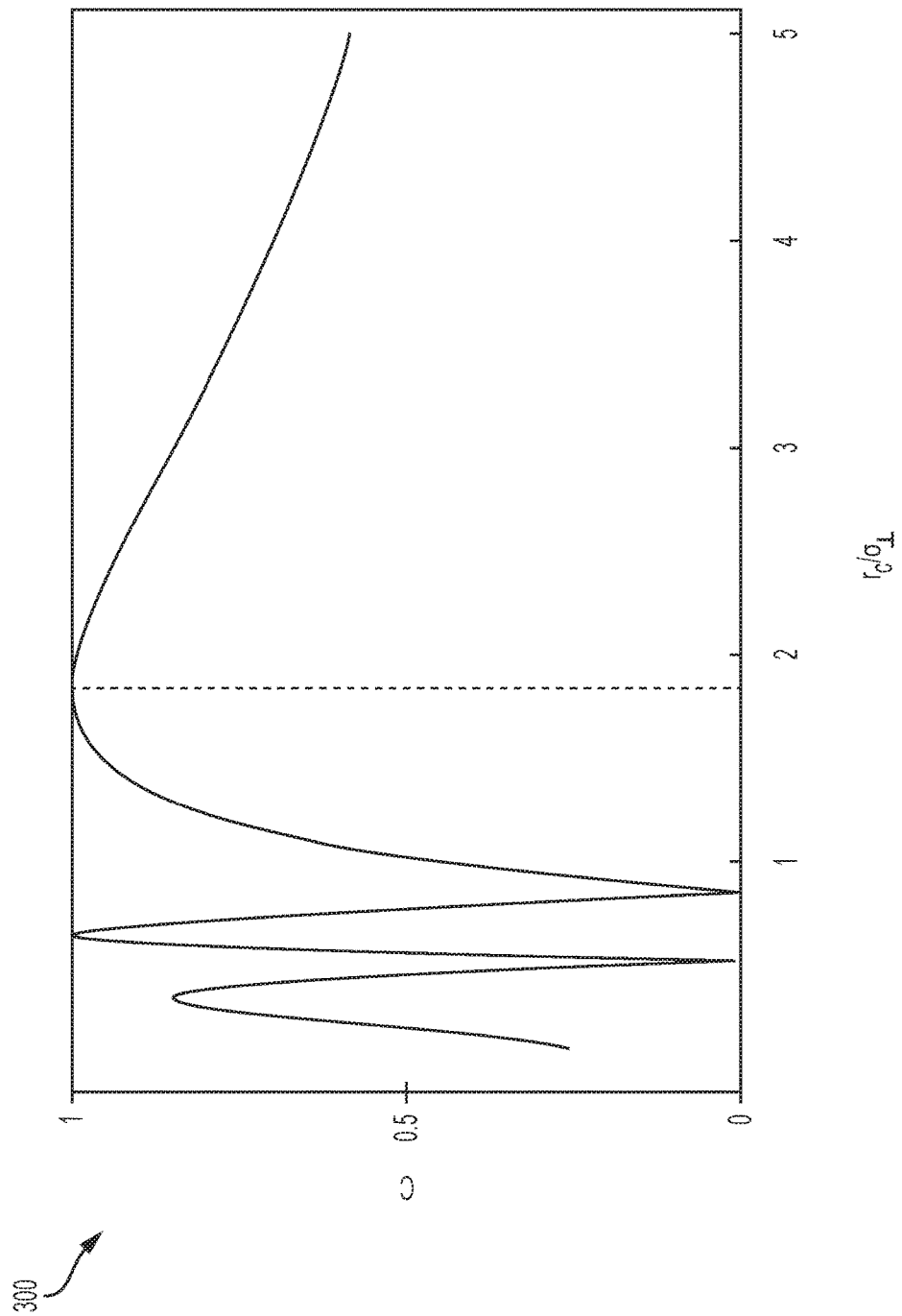
FIG. 3 is a plot showing an example concurrence of a spin-orbit state for the $n_r=0$ subspace of a neutron wave packet.

FIG. 3 is a plot 300 showing an example concurrence of a spin-orbit state for the $n_r = 0$ subspace of a neutron wave packet. In this example, the input state into the quadrupole is $n_{r_i} = 0$, $l_i = 0$. Stronger quadrupole fields correspond to smaller values of $r_c$, and for no quadrupole magnetic field $r_c \rightarrow \infty$.

In the plot 300 shown in FIG. 3, the horizontal axis represents a range of values for the rescaled radial coordinate $\xi = r/\sigma_\perp$, and the vertical axis represents a range of values for the concurrence. In FIG. 3, the concurrence of a pure state is obtained by filtering the neutron wave packet and a single radial quantum number. This subspace concurrence is $$C = 2N_C^2 |C_{n_r, l_i, \uparrow} C_{n_r, l_i+1, \downarrow}|,$$

where $$N_C^2 = \frac{1}{|C_{n_r, l_i, \uparrow}|^2 + |C_{n_r, l_i+1, \downarrow}|^2}$$

is the normalization for each $n_r$ subspace. In the example shown in FIG. 3, the spin orbit concurrence can be maximized for the most probable $n_r = 0$ radial subspace when there is a $\pi$ spin rotation over 1.82 times the coherence length of the wave packet. An example of this condition is represented by the vertical dashed lines in the plots 200, 300 shown in FIGS. 2 and 3, respectively.

In an example implementation, the quadrupole magnetic field can be generated by a configuration of NdFeB magnets that have a surface field of around 0.7 Tesla (T). The quadrupole magnetic field has an axial length (in the z-direction) of 10 centimeter (cm), and a magnetic field gradient strength (in the transverse direction) of 13.8 T/cm. These example parameters can satisfy the $r_c=1.82\,\sigma_\perp$ condition for neutron wave packets having a wavelength of $\lambda=0.271$ nanometers (nm) and a transverse coherence length of $\sigma_\perp=100$ nanometers (nm). In this example, the distance between magnet surfaces can be 2 millimeters (mm) when arranged into the quadrupole geometry. With the 0.7 T surface field of NdFeB magnets, this gradient corresponds to an inner quadrupole gap of around 1 mm. The successful preparation of the entangled state could be verified, for example, by using a Ramsey Fringe experiment.

In a general aspect of the subject matter described above, a spin-orbit state of a neutron wave packet is prepared.

In a first example, an initial state of a neutron wave packet is prepared. The neutron wave packet in the initial state has a spin angular momentum that is polarized in an axial direction. The neutron wave packet in its initial state is directed toward a quadrupole magnetic field. The neutron wave packet passes through the quadrupole magnetic field, which couples the spin angular momentum of the neutron wave packet with an orbital angular momentum of the neutron wave packet. A spin-orbit state of the neutron wave packet is produced from the quadrupole magnetic field, as a result of the interaction between the neutron wave packet and the quadrupole magnetic field.

Implementations of first example may include one or more of the following features. Producing the spin-orbit state comprises producing an entangled spin-orbit state of the neutron wave packet from the quadrupole magnetic field, the neutron wave packet in the entangled spin-orbit state comprising the spin angular momentum entangled with the orbital angular momentum Implementations of first example may include one or more of the following features. One or more parameters of the spin-orbit state are controlled based on a duration of time that the neutron wave packet passes through the quadrupole magnetic field. The neutron wave packet propagates in the axial direction, and the quadrupole magnetic field varies in transverse directions perpendicular to the axial direction. The neutron wave packet is directed, in the axial direction, through the quadrupole magnetic field, along a central axis defined by the quadrupole magnetic field.

Implementations of first example may include one or more of the following features. The initial state of the neutron wave packet is generated by a supermirror configuration. The quadrupole magnetic field is generated by a permanent magnet configuration. The neutron wave packet is directed from the quadrupole magnetic field into a sample material that interacts with the spin-orbit state of the neutron wave packet. An output state of the neutron wave packet is produced from the sample material.

Implementations of first example may include one or more of the following features. The quadrupole magnetic field defines a magnetic field length in the axial direction and a magnetic field gradient strength in a transverse direction, and the neutron wave packet has a wavelength. One or more parameters of the spin-orbit state are controlled by the magnetic field length, the magnetic field gradient strength and the wavelength. The magnetic field length and the magnetic field strength are controlled to produce, for a specified value of the wavelength, a specified concurrence between a spin angular momentum degree of freedom and an orbital angular momentum degree of freedom. The magnetic field length and the magnetic field strength are configured to optimize, for a specified value of the wavelength, a concurrence between a spin angular momentum degree of freedom and an orbital angular momentum degree of freedom. The quadrupole magnetic field is configured such that $r_c=1.82\,\sigma_\perp$ for the neutron wave packet, where $r_c$ represents the radius at which a neutron spin undergoes a spin flip on passing through the length of the quadrupole magnetic field, and $\sigma_\perp$ represents the neutron wave packet transverse coherence length.

In a second example, a system includes a neutron source and a magnet system. The neutron source is configured to generate an initial state of a neutron wave packet on a neutron path. In the initial state a spin angular momentum of the neutron wave packet is polarized in an axial direction. The magnet system is configured to generate a quadrupole magnetic field on the neutron path. The quadrupole magnetic field configured to couple the spin angular momentum of the neutron wave packet with an orbital angular momentum of the neutron wave packet. The magnet system is configured to produce a spin-orbit state of the neutron wave packet on the neutron path.

Implementations of second example may include one or more of the following features. The spin-orbit state is an entangled state, in which the spin angular momentum of the neutron wave packet is entangled with the orbital angular momentum of the neutron wave packet.

Implementations of second example may include one or more of the following features. The magnet system controls a magnetic field length of the quadrupole magnetic field in the axial direction and a magnetic field gradient strength of the quadrupole magnetic field in a transverse direction, and the neutron wave packet has a wavelength. One or more parameters of the spin-orbit state are determined by the magnetic field length, the magnetic field gradient strength and the wavelength. The neutron source directs the neutron wave packet along the neutron path in the axial direction, and the magnet system defines the quadrupole magnetic field components in transverse directions perpendicular to the axial direction. The neutron source directs the neutron wave packet along the neutron path in the axial direction, through the quadrupole magnetic field, along a central axis defined by the quadrupole magnetic field.

Implementations of second example may include one or more of the following features. The system includes a sample material that interacts with the spin-orbit state of the neutron wave packet and produces an output state of the neutron wave packet. The magnet system includes one or more permanent magnets configured to generate the quadrupole magnetic field. The neutron source includes one or more supermirrors configured to polarize the spin angular momentum of the neutron wave packet on the neutron path.

In a third example, a spin-polarized state of a neutron wave packet is generated on a neutron path by operation of a neutron source. A quadrupole magnetic field is applied to the neutron wave packet on the neutron path by operation of a magnet system. A spin-orbit state of the neutron wave packet is produced from the magnet system on the neutron path.

In a fourth example, spin-orbit states of neutrons are performed. Spin-polarized neutrons pass through the center of a quadrupole magnetic field gradient, which creates a spin-orbit coupling. For a given neutron wave packet transverse coherence length, the quadrupole magnetic gradient and the quadrupole length can be chosen to optimize the concurrence between the spin and orbit degrees of freedom. The optimization condition can be, for example, $r_c=1.82\,\sigma_\perp$, where $r_c$ is the radius at which the spin undergoes a spin flip on passing through the length of the quadrupole, and $\sigma_\perp$ is the neutron wave packet transverse coherence length.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the following claims.

What is claimed is:

1. A method comprising:
    generating an initial state of a neutron wave packet, the neutron wave packet in the initial state comprising a spin angular momentum that is polarized in an axial direction;
    directing the neutron wave packet through a quadrupole magnetic field that couples the spin angular momentum of the neutron wave packet with an orbital angular momentum of the neutron wave packet; and
    producing a spin-orbit state of the neutron wave packet from the quadrupole magnetic field.

2. The method of claim 1, wherein producing the spin-orbit state comprises producing an entangled state of the neutron wave packet from the quadrupole magnetic field, the neutron wave packet in the entangled state comprising the spin angular momentum entangled with the orbital angular momentum.

3. The method of claim 1, comprising controlling a parameter of the spin-orbit state based on a duration of time that the neutron wave packet passes through the quadrupole magnetic field.

4. The method of claim 1, wherein the quadrupole magnetic field has a magnetic field length in the axial direction and a magnetic field gradient strength in a transverse direction, the neutron wave packet has a wavelength, and a parameter of the spin-orbit state is controlled by the magnetic field length, the magnetic field gradient strength and the wavelength.

5. The method of claim 4, wherein the magnetic field length and the magnetic field strength are controlled to produce, for a specified value of the wavelength, a specified concurrence between a spin angular momentum degree of freedom and an orbital angular momentum degree of freedom.

6. The method of claim 4, wherein the magnetic field length and the magnetic field strength are configured to optimize, for a specified value of the wavelength, a concurrence between a spin angular momentum degree of freedom and an orbital angular momentum degree of freedom.

7. The method of claim 1, comprising:
    directing the neutron wave packet from the quadrupole magnetic field into a sample material that interacts with the spin-orbit state of the neutron wave packet; and
    producing an output state of the neutron wave packet from the sample material.

8. The method of claim 1, comprising generating the quadrupole magnetic field by a permanent magnet configuration.

9. A system comprising:
    a neutron source configured to generate an initial state of a neutron wave packet on a neutron path, the neutron wave packet in the initial state comprising a spin angular momentum that is polarized in an axial direction; and
    a magnet system configured to:
        generate a quadrupole magnetic field on the neutron path, the quadrupole magnetic field configured to couple the spin angular momentum of the neutron wave packet with an orbital angular momentum of the neutron wave packet; and
        produce a spin-orbit state of the neutron wave packet on the neutron path.

10. The system of claim 9, the spin-orbit state comprising an entangled state in which the spin angular momentum of the neutron wave packet is entangled with the orbital angular momentum of the neutron wave packet.

11. The system of claim 9, wherein the magnet system controls a magnetic field length of the quadrupole magnetic field in the axial direction and a magnetic field gradient strength of the quadrupole magnetic field in a transverse direction, the neutron wave packet has a wavelength, and a parameter of the spin-orbit state is determined by the magnetic field length, the magnetic field gradient strength and the wavelength.

12. The system of claim 9, wherein the neutron source directs the neutron wave packet along the neutron path in the axial direction, and the magnet system defines the quadrupole magnetic field components in transverse directions perpendicular to the axial direction.

13. The system of claim 9, wherein the neutron source directs the neutron wave packet along the neutron path in the axial direction, through the quadrupole magnetic field, along a central axis defined by the quadrupole magnetic field.

14. The system of claim 9, comprising a sample material that interacts with the spin-orbit state of the neutron wave packet and produces an output state of the neutron wave packet.

15. The system of claim 9, wherein the magnet system comprises one or more permanent magnets configured to generate the quadrupole magnetic field.

16. The system of claim 9, comprising one or more supermirrors configured to polarize the spin angular momentum of the neutron wave packet on the neutron path.

17. A method comprising:
    generating, by operation of a neutron source, a spin-polarized state of a neutron wave packet on a neutron path;
    applying, by operation of a magnet system, a quadrupole magnetic field to the neutron wave packet on the neutron path; and
    producing, from the magnet system, a spin-orbit state of the neutron wave packet on the neutron path.

18. The method of claim 17, wherein the quadrupole magnetic field couples the spin angular momentum of the neutron wave packet with an orbital angular momentum of the neutron wave packet.

19. The method of claim 17, wherein the spin-orbit state comprises an entangled spin-orbit state.

* * * * *

UNITED STATES PATENT AND TRADEMARK OFFICE
CERTIFICATE OF CORRECTION

PATENT NO. : 10,215,715 B1
APPLICATION NO. : 15/277190
DATED : February 26, 2019
INVENTOR(S) : David G. Cory et al.

Page 1 of 1

It is certified that error appears in the above-identified patent and that said Letters Patent is hereby corrected as shown below:

In the Specification

Column 2, Detailed Description, Line 36, After "number,", insert -- $\mathcal{L}_{n_r}^{|\ell|}(\xi^2)$ --

Column 8, Detailed Description, Lines 22-23, Delete "$\rho_{so} = |\psi_{so}\rangle\langle\psi_{so}|,$" and insert -- $\rho_{so} = |\psi_{so}\rangle\langle\psi_{so}|,$ -- therefor Column 8, Detailed Description, Line 25, Delete "$\mathcal{C}(|\psi_{so}\rangle) = \sqrt{2(1-Tr[\rho_s^2])},$" and insert -- $\mathcal{C}(|\psi_{so}\rangle) = \sqrt{2(1-Tr[\rho_s^2])},$ -- therefor Column 8, Detailed Description, Lines 27-28, Delete "$\rho_s = Tr_o[|\psi_{so}\rangle\langle\psi_{so}|]$" and insert -- $\rho_s = Tr_o[|\psi_{so}\rangle\langle\psi_{so}|]$ -- therefor Column 8, Detailed Description, Line 32, Delete "$\mathcal{X} = 0.97$" and insert -- $\mathcal{C} = 0.97$ -- therefor Signed and Sealed this
Twenty-fifth Day of June, 2019

Andrei Iancu
*Director of the United States Patent and Trademark Office*